United States Patent
Guibert et al.

Patent Number: 5,443,487
Date of Patent: * Aug. 22, 1995

[54] COMBINED CHEMO-THERMO THERAPY TECHNIQUE

[76] Inventors: Raul Guibert; Bettina Guibert, both of 750 S. Bundy Dr., Apt. 101, Brentwood, Calif. 90049

[*] Notice: The portion of the term of this patent subsequent to May 31, 2011 has been disclaimed.

[21] Appl. No.: 169,356

[22] Filed: Dec. 20, 1993

Related U.S. Application Data

[63] Continuation-in-part of Ser. No. 26,756, Mar. 5, 1993, Pat. No. 5,315,994.

[51] Int. Cl.6 ............................................. A61F 7/00
[52] U.S. Cl. ...................................................... 607/101
[58] Field of Search ............................................. 607/101

[56] References Cited

U.S. PATENT DOCUMENTS

| | | | |
|---|---|---|---|
| Re. 19,724 | 10/1935 | Martin | 128/362 |
| 1,903,427 | 6/1930 | Martin | 128/400 |
| 2,062,992 | 1/1936 | Martin | 34/100 |
| 2,133,078 | 10/1938 | Carter | 34/100 |
| 2,197,752 | 8/1938 | Kallmann | 34/100 |
| 2,232,156 | 2/1941 | Abeles | 128/399 |
| 2,334,056 | 11/1943 | Anderson | 219/400 |
| 2,542,699 | 2/1951 | Oliver | 219/400 |
| 3,082,540 | 3/1963 | Hiltenbrand | 34/100 |
| 3,516,411 | 5/1968 | Adler | 128/399 |
| 3,816,940 | 6/1974 | Cournoyer | 34/100 |
| 4,398,535 | 8/1983 | Guibert | 128/399 |
| 4,461,299 | 7/1984 | Guibert | 128/399 |
| 4,595,008 | 6/1986 | Guibert | 128/399 |
| 4,667,658 | 5/1987 | Guibert | 128/400 |
| 4,671,788 | 1/1987 | Wu | 128/399 |
| 5,107,832 | 4/1992 | Guibert et al. | 128/399 |
| 5,131,904 | 7/1992 | Markoll | 600/14 |
| 5,190,031 | 3/1993 | Guibert et al. | 128/399 |
| 5,315,994 | 5/1994 | Guibert et al. | 607/101 |

Primary Examiner—William H. Grieb
Attorney, Agent, or Firm—Michael Ebert

[57] ABSTRACT

A combined chemo-thermo therapy technique in which a pharmaceutical agent, such as a lipolysis cream, is topically applied to a localized skin surface overlying a problem region to be treated. This surface is then subjected to an air stream whose temperature alternates periodically from a high peak level to a lower base level in a pulsatory heat energy wave pattern. Because heat transfer takes place under the skin in the intervals between successive peaks, the temperature of the problem region is significantly raised, but that on the skin surface remains at a tolerable level. As a consequence, the absorption of the agent and its diffusion throughout the tissues of the heated problem region is accelerated and its interaction therewith is promoted to enhance the effectiveness of the treatment.

9 Claims, 2 Drawing Sheets

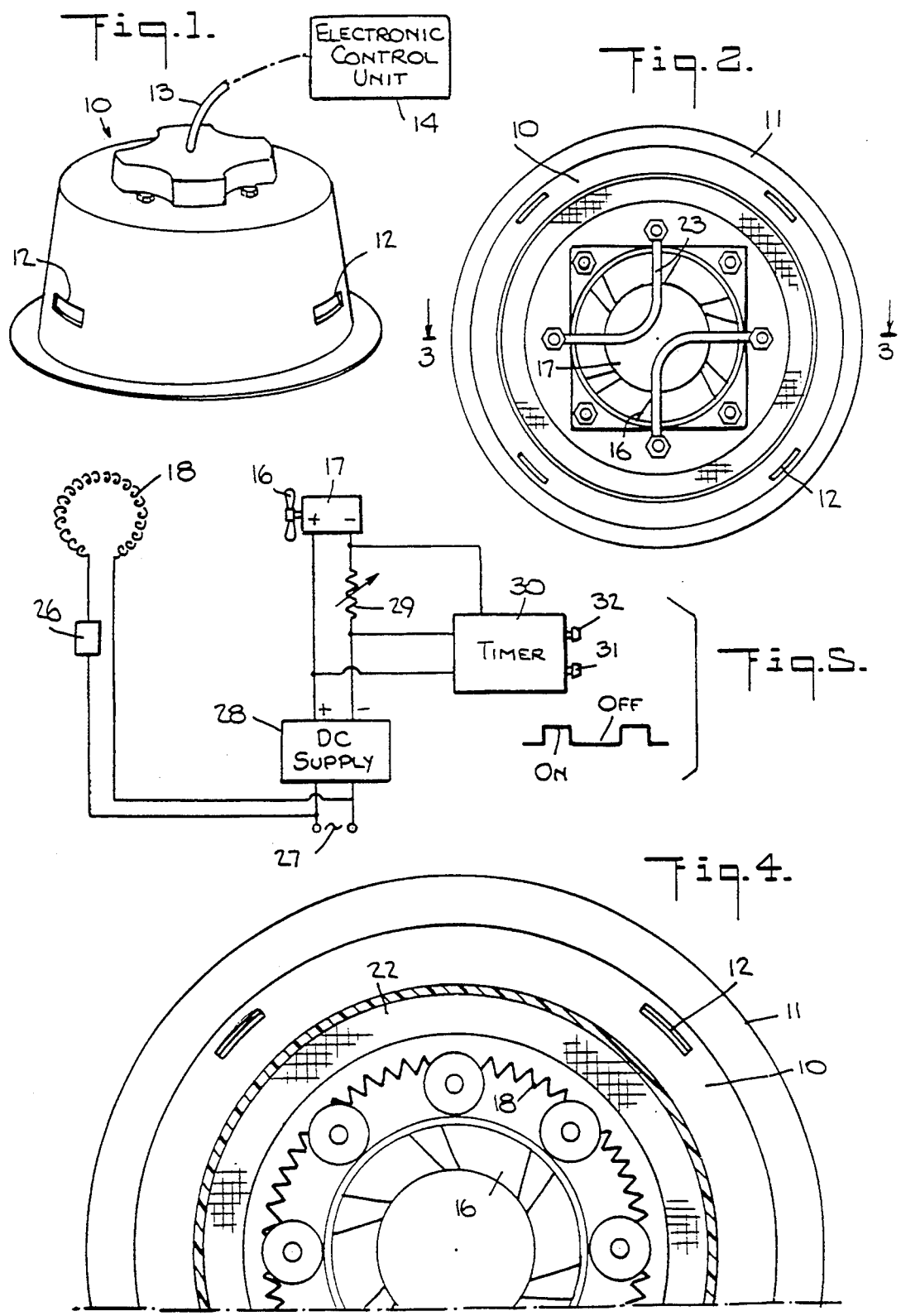

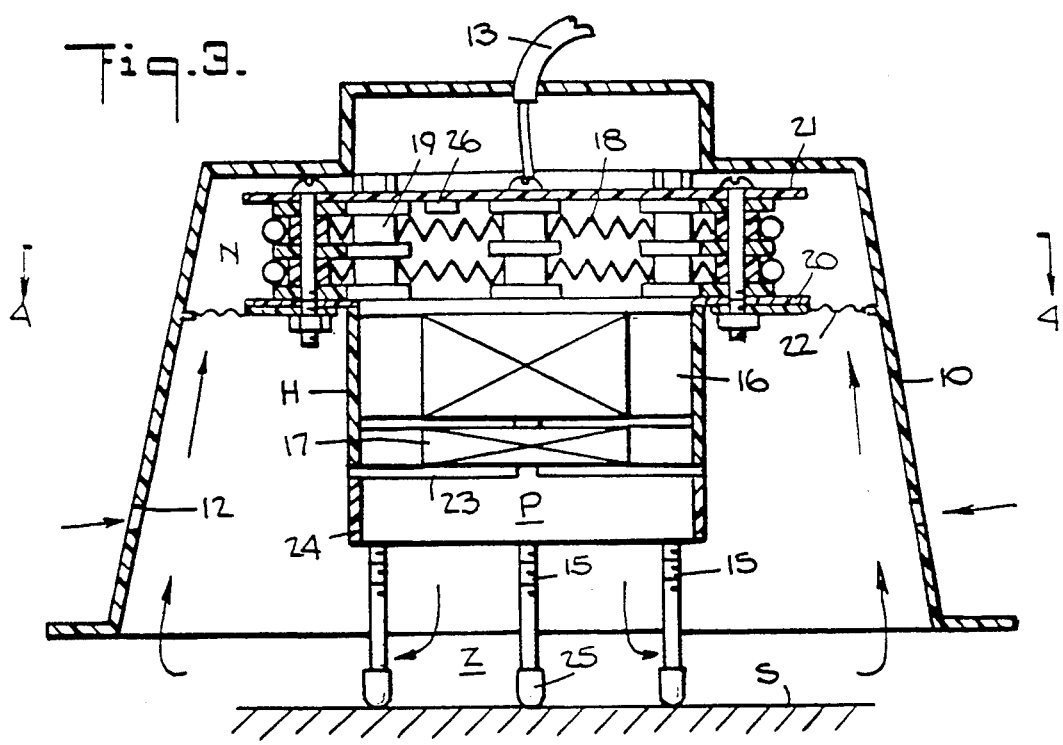
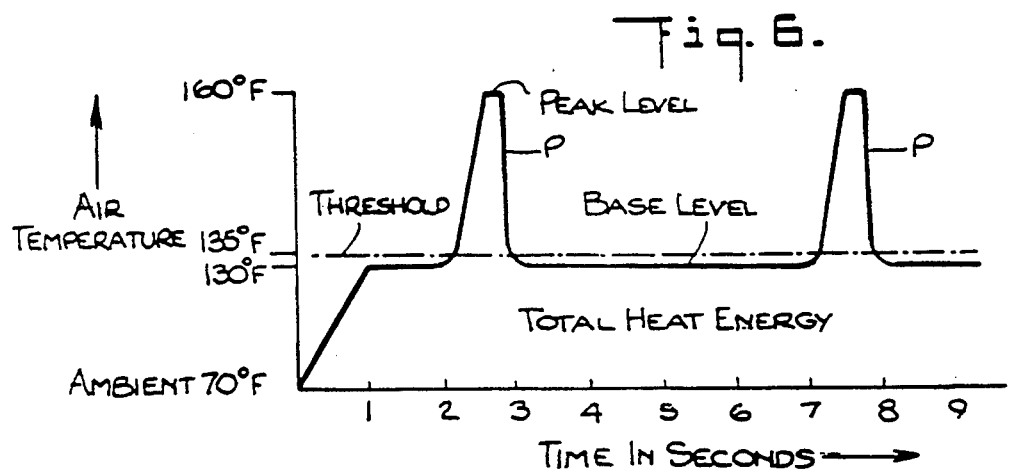
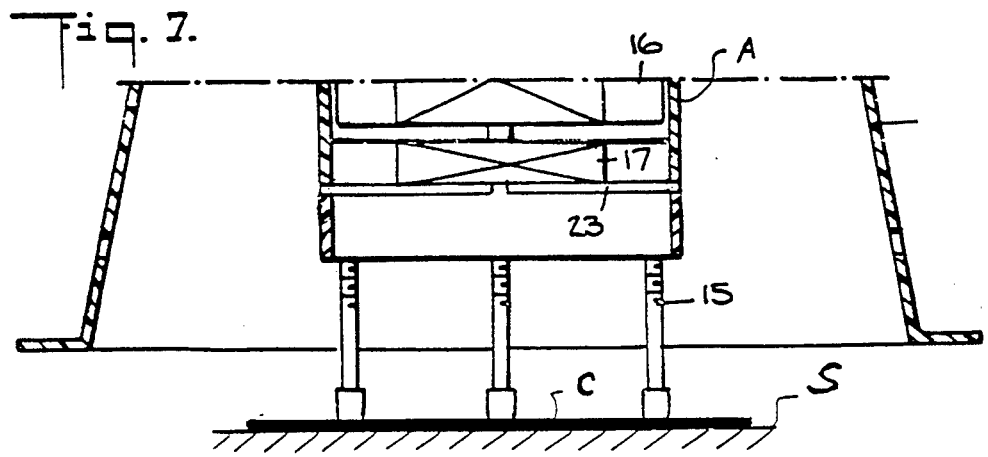

COMBINED CHEMO-THERMO THERAPY TECHNIQUE

RELATED APPLICATIONS

This application is a continuation-in-part of our application entitled "Combined Thermotherapy and Electrotherapy Technique," Ser. No. 08/026,756, filed Mar. 5, 1993, now U.S. Pat. No. 5,315,994.

BACKGROUND OF THE INVENTION

1. Field of Invention

This invention relates generally to the treatment of patients with both a pharmaceutical agent applied topically to the skin and with heat, and more particularly to a combined chemo-thermo therapy technique in which heat acts to accelerate the absorption and diffusion of the agent and to promote its interaction with the tissue in the problem region of the body being treated.

2. Status of Prior Art

The term "problem region," as used herein, refers to a tumor, a set of muscles, or any other tissue site underlying the skin which is causing difficulty and which lends itself to treatment.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a warmed substance; that is, by conduction, or by radiating energy into the body.

As pointed out in chapter 10, "Therapeutic Heat" in the text Therapeutic Heat and Cold, edited by Justuf F. Lehmann and published in 1982 by Williams and Wilkins, it is generally accepted that heat produces desirable therapeutic effects, for it increases the extensibility of collagen tissues, it decreases joint stiffness, and it affords pain relief. Moreover, heat relieves muscular spasms, it aids in the resolution of inflammatory infiltrates, edema and exudates, and it enhances blood flow.

The difficulty heretofore experienced in effectively applying heat to a patient is that when transferring heat inwardly through living tissue to a problem region underlying the skin, if the heat applied to the skin surface is within a tolerable temperature range, then not enough heat energy is transferred to this site to afford beneficial effects.

As indicated in the Lehmann text, superficial heat is commonly tied in with various forms of heating media such as a paraffin bath, hot air or hot water and radiant heat (infrared). For a given patient, the temperature sensitivity threshold is that temperature level of the heating medium to which the patient is exposed, above which the patient experiences undue discomfort. Thus temperature levels of the medium below the sensitivity threshold are more or less tolerable, whereas those above the threshold are effectively intolerable. If, for example, a patient being subjected to thermotherapy finds that the heat is more than he can stand and wishes the procedure discontinued, clearly the heat of the medium to which he is exposed is above his sensitivity threshold.

One must bear in mind that the temperature sensitivity threshold is determined on the basis of continuous exposure to the heating medium, for one can tolerate much higher heat levels when one is only exposed momentarily or intermittently to high temperatures.

The temperature sensitivity threshold depends on the nature of the heating medium. Thus, as noted in the Lehmann text, when the medium is hot water which is at the same temperature and is applied to the patient in the same fashion as heated paraffin which has a low heat capacity, the paraffin can be tolerated by a patient but the hot water is intolerable for it has a high specific heat and a high order of thermal conductivity.

As a consequence, with conventional heating techniques, regardless of the medium used, when the patient is continuously exposed to a heating medium which is at a substantially constant temperature level, though this level is high enough to bring about adequate heat transfer to the problem region underlying the exposed skin, then the skin temperature is usually well above the tolerable level and this may result in extreme discomfort to the patient and even to the burning of tissue.

Because in all conventional heat applicators, the heat is applied continuously to the skin area overlying the problem region, this imposes strict limits on the acceptable temperature level. Thus if one seeks to have the heat penetrate more deeply into the body, the temperature at the surface area must be raised to promote more rapid heat transfer, for the higher the differential between the internal and external temperatures, the greater the rate of transfer. But a point is then quickly reached at which the patient is made uncomfortable for one can only tolerate continuously applied heat whose temperature level is not excessively above body temperature. The temperature sensitivity threshold for a given patient is that temperature level of the heating medium to which the patient is continuously exposed above which the patient experiences serious discomfort.

The prior Guibert U.S. Pat. No. 4,667,658 and our above-identified application disclose a technique for applying therapeutic heat to a skin surface area of a patient whose threshold of sensitivity is determined by that temperature level of the heating medium to which the patient is continuously exposed, above which the patient experiences discomfort or injury. In this technique, the skin surface is exposed to a heating medium whose temperature is at a base level that is well above ambient bug no higher than the temperature sensitivity threshold, the temperature of the medium being periodically raised above the base level to create high heat energy pulses whose peak temperatures are much higher than the threshold.

The duty cycle of these pulses is such as to allow for internal heat transfer to take place in the region below the exposed area of the patient in the intervals between pulses to an extent preventing an excessive rise in temperature at the skin surface whereby the patient gains the benefit of high heat energy treatment without discomfort or injury.

The topical application of a pharmaceutical cream, ointment or other agent to the surface of the skin overlying a problem region for the purpose of relieving pain or to alleviate an abnormal condition is commonplace. It is also known to adhere a patch to the skin, the patch being impregnated with a pharmaceutical agent that is absorbed and penetrates the tissue underlying the skin to interact therewith.

The present invention involves the application of heat energy to the same skin surface to which a pharmaceutical agent has been applied, the heat acting to render the tissue of the problem region more conducive to interaction with the agent. The present invention will be described in conjunction with a lipolysis cream that when applied to the skin in the area of the thighs, hips or buttocks, is absorbed and diffused throughout the tissues underlying the skin to bring about a reduction in cellulite fat deposits in these regions. It is to be understood, however, that this invention is by no means limited to a lipolysis cream and is unseable with any cream or ointment applied to the skin or to patch adhered to the skin in which the interaction of the pharmaceutical agent which is absorbed by the skin and penetrates the underlying tissue region is accelerated and promoted by the application of pulsed heat to the same surface.

U.S. Pat. No. 4,525,359 discloses a lipolysis cream which when applied to the skin in the hip, thigh or buttocks area, then penetrates the underlying tissue and interacts with fat deposits therein to bring about a reduction in these deposits, thereby reducing the weight of the individual body treated.

As pointed out in this patent, the in vivo neurological control of lipolysis in the fat cells is so organized that activity of the beta adrenergic receptor stimulates lipolysis, that is the hydrolysis of fat. An agent which activates the beta adrenergic receptor encourages lipolysis and results in the reduction in size of the fat cells. The beta adrenergic stimulator is selected from a group including theophylline, isoproternal, forskolin and eponephrine.

SUMMARY OF INVENTION

In view of the foregoing, the main object of this invention is to provide a chemo-thermo therapy technique in which applied to a localized skin surface of a patient to be treated is a pharmaceutic agent which is absorbed by the skin and penetrates the tissues in the region underlying the skin surface, the same surface then being exposed to a stream of air having a pulsatory heat energy which acts to raise the temperature of the tissues underlying the skin and to accelerate and promote the interaction of the agent with the tissues.

A significant advantage of the invention, when used in conjunction with a lipolysis cream, is that it results in a greater reduction in cellulite fat deposits in the thighs, hips and buttocks of the individual being treated, without however, in any way damages the skin surface.

Also an object of the invention is to provide a self-sufficient heat applicator which is portable and can be rested against the skin surface after a cream, ointment or other pharmaceutic agent has been applied or adhered thereto, so as to subject the skin to a stream of air having a pulsatory heat energy pattern to render the region being treated by the agent more conducive thereto.

Briefly stated, these objects are obtained by a combined chemo-thermo therapy technique in which a pharmaceutical agent, such as a lipolysis cream, is topically applied to a localized skin surface overlying a problem region to be treated. This surface is then subjected to an air stream whose temperature alternates periodically from a high peak level to a lower base level in a pulsatory heat energy wave pattern. Because heat transfer takes place under the skin in the intervals between successive peaks, the temperature of the problem region is significantly raised, but that on the skin surface remains at a tolerable level. As a consequence, the absorption of the agent and its diffusion throughout the tissues of the heated problem region is accelerated and its interaction therewith is promoted to enhance the effectiveness of the treatment.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of a thermotherapy applicator in accordance with the invention;

FIG. 2 is a bottom view of the applicator;

FIG. 3 is a longitudinal section taken in the plane indicated by line 3—3 in FIG. 2;

FIG. 4 is a transverse section taken in the plane indicated by line 4—4 in FIG. 3;

FIG. 5 illustrates in block diagram the electrical control system for the applicator;

FIG. 6 is a graph illustrative of the temperature pattern of the heat produced by the applicator; and FIG. 7 is a sectional view showing the applicator operating in a combined chemo-thermo therapy technique in accordance with the invention.

DESCRIPTION OF INVENTION

The Applicator

Referring now to FIGS. 1 to 2, there is shown an applicator according to the invention, the applicator including a dome-shaped casing 10 molded of high-strength, fire retardant, synthetic plastic material having electrical insulating properties. Suitable for this purpose is purpose is polycarbonate. Casing dome 10 has an open base surrounded by a circular flange 11. In practice, fitted onto this flange is an annular ring of elastomeric material which acts as a protective cushion when the applicator is applied to the skin of the patient being treated. Formed in the wall of the dome and adjacent flange 11 is a circular series of air-inlet ports 12 of predetermined size. The applicator is coupled by a flexible cable 13 to an electrical control unit 14 which supplies operating power to the electrical heater and to the fan motor included in the applicator.

As shown in FIGS. 3 and 4, supported coaxially within casing dome 10 at an intermediate position therein by threaded mounting rods 15 is a tube axial fan 16 supported on the shaft of a miniature DC motor 17, the fan and motor being contained with a cylindrical housing H.

Coaxially mounted above fan 16 in the dome is an electric heater ring 18 formed of a helical coil of resistance wire wound about a circular array of ceramic stand off insulators 19 sandwiched between lower and upper annular insulation plates 20 and 21.

When fan motor 17 is energized, the rotating fan creates a negative pressure region N in the upper dome space occupied by heater 18, and a positive pressure region P below the fan. An annular protective screen or mesh 22 extends between the lower plate 20 and the wall of the dome to block access of foreign elements to the heater ring. A protective wire guard 23 is interposed between motor 17 and a collar 24 attached thereto which is aligned with cylindrical housing H and blocks access to the fan.

Threaded rods 15 which support the fan motor and the heater ring and the collar attached thereto extend from the roof of the dome and terminate in feet 25 of elastomeric cushioning material. These feet serve, as shown in FIG. 3, to maintain the applicator in spaced relation from the localized skin surface S of a patient to be treated, thereby creating in this relatively narrow space a turbulent air flow zone Z. Supported on the underside of annular insulation plate 21 is a heat sensor 26, preferably in the form of a bi-metallic switch, such as a Klixon switch marketed by Texas Instruments Company, to protect the applicator should it become overheated for any reason.

In operation, because of the negative pressure in region N in the dome, air is drawn from flow zone Z below the open base of the dome into this region. At the same time, some outside air is drawn into the negative pressure region N through ports 12, as indicated by the arrows in FIG. 3.

The air drawn into negative pressure region N passes through heater ring 18 and is heated thereby to a uniform temperature before being propelled by the fan into the positive pressure zone P, from which the heated air is discharged into flow zone 1 where it acts to apply heat to skin surface S. From this zone, a substantial percentage of the heated air returns to the negative pressure zone, thereby creating a circulatory loop from which little heated air escapes into the atmosphere surrounding the applicator.

It is to be noted that the tube axial fan projects a column of air at a uniform temperature into the positive pressure region P, and that this column is surrounded by air drawn from flow zone Z in the positive pressure region. Because of collar 24 there is no interference therebetween.

Hence with an applicator in accordance with the invention, it becomes possible to recirculate a substantial percentage of the heated air and thereby eliminate major heat losses. And it becomes possible to pulsate the flow of air projected into air flow zone Z without pulsating the power applied to the heater element, so that this power is maintained constant during the base and peak phases of the pulsatory heat wave applied to the patient. And with an applicator in accordance with the invention, the ambient temperature of the room in which the applicator is operating undergoes no significant increase, for substantially all of the heat energy generated by the applicator is exploited.

Electronic control unit 14 functions to apply AC operating power (i.e., 12 volts 60 cycle AC) to electric heater ring 18 and to control this power so that the temperature of the air applied to a patient being treated can be tolerated by the patient, bearing in mind that no two patients have exactly the same threshold sensitivity and that some patients are rendered uncomfortable at temperatures which are acceptable to others. In practice, therefore, it is desirable that the control unit be capable of being adjusted to effect temperature changes in small increments.

While heater 18 is being energized, the DC fan motor 17 has an operating voltage applied thereto which changes periodically from the rated voltage of motor 17 to a lower voltage level. Thus if the rated voltage for the fan motor is 12 volts DC, at which voltage the fan then operates at high velocity, and the voltage applied to the motor changes periodically from 12 volts to 8 volts DC, then the fan velocity will go periodically from high to low.

It is important to understand the relationship between the velocity of air passing through the heater coil ring from its outer periphery to its inner periphery and the amount of heat imparted to this air by the heater.

When the fan is operating at high velocity, as a consequence of which the air passes quickly through the heater ring, then the amount of heat imparted to the air in the course of its transit through the coil will be small, resulting in a relatively low rise in air temperature. When, however, the fan is operating at low velocity and the air then passes slowly through the heater coil ring, then more heat will be imparted to the air in the course of its transit through the heater coil. This will result in a relatively high rise in air temperature.

In the applicator, when the motor operates at its rated voltage, the fan velocity is then high and the air is heated to a base level above ambient temperature but somewhat below the temperature sensitivity of the patient. When the motor operates at below its rated voltage and the fan velocity is low, the air is then heated to an elevated peak temperature level well above the base temperature level. The relationship of the base and peak temperature levels to the sensitivity threshold of a patient will now be considered in connection with the thermotherapy technique carried out by the applicator.

The applicator applies heat energy to a localized skin surface area of a patient overlying a problem region. The air stream passing through zone Z has a temperature in the intervals when the velocity of the air stream is high is at a substantially constant base level which is well above ambient but somewhat below the sensitivity threshold of the patient. In the intervals in which the velocity of the air stream is low, its temperature is then elevated to reach a peak level well above the base level. Thus if the temperature were maintained at this peak level for, say, a minute or more, though it would then act to promote rapid inward heat transfer to the problem region in the body, it would at the same time cause extreme discomfort and possible injury to the patient.

In order, therefore, to render the applied heat energy tolerable and at the same time bring about a rapid inward heat transfer from the skin area to the problem region, the heat energy in a technique in accordance with the invention is applied in a pulsatory thermal wave pattern.

In a technique in accordance with the invention, a stream of air is projected toward a limited skin area of the patient being treated in zone Z. The air temperature which is drawn from the atmosphere is initially at ambient (i.e., 70° F.). When the velocity of the air as controlled by the fan is high, then the air is heated to a constant base temperature level (i.e., 130° F.) which is well above ambient (70° F.) but somewhat below temperature sensitivity threshold of the patient (i.e., 135° F.).

The temperature of the air stream is periodically raised well above its base level by heat energy pulses to a peak level (i.e., 160° F.), which is much higher than the sensitivity threshold. This rise in temperature takes place when the air velocity, as controlled by the fan, is low.

The resultant pulsatory thermal air wave pattern is such that the stream of hot air at the base temperature level is blown toward the localized skin area to impinge thereon and to flow across the area in zone Z. This air stream is periodically raised in temperature to a peak level so that the localized skin area being subjected to treatment is exposed to high temperature heat energy well above the sensitivity threshold for no more than a brief period insufficient to cause discomfort, followed by an interval at the markedly lower base temperature level during which rapid heat transfer takes place through the body tissue toward the problem region. This inward transfer acts to reduce the temperature at the surface to a degree preventing a significant rise thereof above the sensitivity threshold.

In FIG. 6 temperature is plotted against time in one second increments. It will be seen that the temperature of the air stream is periodically raised well above its base level (130° F.) by heat energy pulse to a peak level (160° F.) which is much higher than the sensitivity threshold.

A technique in accordance with this invention makes it possible to produce a much greater rise in the temperature of an internal problem region underlying a limited skin area subjected to the heat without, however, discomfort to the patient or damage to the tissue being heated. Because the internal heat is significantly higher in temperature than that heretofore obtainable without discomfort or damage, the beneficial effects are far more pronounced.

FIG. 5 shows one preferred embodiment of the electronic control unit 14 which in FIG. 1 is remote from the applicator 10. The unit is connected to an AC power line 27 (i.e., 120 volts AC, 60 Hz), and it supplies this voltage through bi-metallic switch 26, which, as explained previously, acts to cut off the heater if for any reason the temperature within the applicator reaches an excessive level.

The AC power line voltage is also applied to a DC supply 28 which includes a step-down transformer and a full-wave rectifier to produce an output DC voltage whose level matches the rated voltage of the fan motor 17. Hence if the rated voltage is 12 V DC, then this is the output voltage of DC supply 28. Motor 17 operates at its maximum RPM when energized at a voltage below its rated voltage.

Connected in series between the output of DC supply 28 and the input terminals of fan motor 17 is a variable resistor 28 which is adjustable to produce a voltage at the input terminals of the motor which is below the rated motor voltage, say, 8 volts DC, in which event the motor when energized at the reduced voltage level will turn fan 16 at a low velocity. If the voltage is, say, 6.5 volts, the velocity will be still lower.

Also connected to the output of DC supply 28 is a repeat cycle timer 30 having control knobs 31 and 32 for independently adjusting the on-off timer and hence the duty cycle. Thus the time range may be 1 to 20 seconds for the "off" period of the timer, and 1 to 20 seconds for its "on" period.

Timer 30 is connected in shunt relation with resistor 29 so that when in the course of each cycle the timer is "on," this acts to short circuit resistor 29, as a result of which the full output of the DC supply 28 is applied to motor 27, and it then operates at its rated voltage to drive fan 16 at high velocity. When in the course of each cycle the timer is "off," then resistor 29 is not short circuited, and a reduced voltage is applied to the motor which then operates to drive the fan at low velocity.

Thus each time timer 30 is "off" and the fan turns at low velocity, the heat produced then reaches the desired peak level well above the base level. But each time timer 30 is "on," the reduced heat then produces, as a result of the high fan velocity, a base level temperature somewhat below the threshold sensitivity of the patient.

Combined Chemo-Thermo Therapy Technique

As shown in FIG. 7, applied topically to the localized skin surface S overlying a problem region is a layer of cream C. For purposes of illustrating the invention, this cream is a lipolysis agent which functions to reduce cellulite fat deposits in the tissues of the problem region. However, as pointed out previously, the agent applied to the skin surface may be a pharmaceutical agent to reduce pain or to alleviate a pathological condition, the effectiveness of the agent depending on how well it interacts with the tissues in the problem region.

In the case of a lipolysis cream such as the cream disclosed in U.S. Pat. No. 4,525,359, after the cream is applied to the skin, its active ingredients diffuse throughout the regional fat deposits in the thigh, hips or buttocks of the patient, depending on the area of application.

In order to accelerate the absorption of the cream into the tissue region underlying the skin surface to which the cream is applied and to promote the interaction of the active ingredients of the cream with the fat deposits, the air stream projected from applicator A is directed toward the surface of the skin coated with the cream. Because of the pulsating heat energy wave pattern of this air stream, the skin surface is heated to a tolerable level above ambient temperature. This heat serves to render the cream coating less viscous and to open the pores of the skin to accelerate the delivery of the cream into the tissues of the problem region underlying the skin surface.

And because of heat transfer which takes place within the tissues underlying the skin in the intervals between the successive peaks of the pulsatory energy wave pattern, the temperature of the problem region is elevated to a substantially greater level than would be possible had continuous heat energy been applied to the skin. The relatively high temperature level of the problem region renders this region highly conducive to interaction with the pharmaceutical agent delivered thereto.

If this agent is a lipolysis cream and effects hydrolysis of fat deposits in the tissue, a significantly greater reduction in weight is achieved than in the absence of heat.

Where the problem region being treated is painful, as a result of an arthritic or other chronic condition, and the pharmaceutical agent applied to the skin surface overlying this region is a pain-relieving agent, then the pulsatory heat energy applied to this surface would not only promote the interaction of the agent with the tissues in the region, but it also itself quite apart from the agent acts to reduce pain. The combined chemo-thermo therapy is synergistic and is especially beneficial in treating intensely painful regions.

While there has been shown a preferred technique in accordance with the invention, it is to be understood that many changes may be made therein without departing from the spirit of the invention.

We claim:

1. A combined chemo-thermo therapy technique comprising the steps of:

A. topically applying to a localized skin surface of a patient overlying a problem region a pharmaceutical agent which when absorbed by the skin and diffused throughout tissues in the problem region interacts therewith to produce beneficial effects; and B. applying to the same skin surface a stream of air whose temperature alternates periodically from a high peak level to a lower base level in a pulsatory heat energy wave pattern which acts to markedly raise the temperature of the problem region without raising the temperature at the skin surface above a tolerable level, whereby the absorption and diffusion of the agent is accelerated and its interaction with the tissues is promoted to enhance the effectiveness of the treatment.

2. A technique as set forth in claim 1, in which the agent is in the form of a cream that is coated on the skin surface.

3. A technique as set forth in claim 2 in which the cream includes active ingredients producing lipolysis of fat cells in the problem region.

4. A technique as set forth in claim 3, in which the cream is applied to a thigh of the patient.

5. A technique as set forth in claim 3, in which the cream is applied to the hips of the patient.

6. A technique as set forth in claim 3, in which the cream is applied to the buttocks of the patient.

7. A technique as set forth in claim 1, in which the pharmaceutical agent impregnates a patch adhered to the skin surface.

8. A technique as set forth in claim 1, in which the peak level is about 160° F.

9. A technique as set forth in claim 8, in which the base level is about 130° F.

* * * * *